United States Patent [19]

Valkirs et al.

[11] Patent Number: 4,727,019
[45] Date of Patent: * Feb. 23, 1988

[54] METHOD AND APPARATUS FOR IMMUNOASSAYS

[75] Inventors: Gunars E. Valkirs, San Marcos; Newton C. Owen, Encinitas; Philip A. Levinson, San Diego, all of Calif.

[73] Assignee: Hybritech Incorporated, San Diego, Calif.

[*] Notice: The portion of the term of this patent subsequent to Dec. 30, 2003 has been disclaimed.

[21] Appl. No.: 733,292

[22] Filed: May 10, 1985

Related U.S. Application Data

[63] Continuation-in-part of Ser. No. 609,395, May 11, 1984, Pat. No. 4,632,901.

[51] Int. Cl.$^4$ .................. G01N 33/53; G01N 33/543
[52] U.S. Cl. .......................................... 435/5; 435/6; 435/7; 435/287; 436/513; 436/518; 436/527; 436/531; 436/548; 436/807; 436/818; 436/820; 436/824
[58] Field of Search ............... 435/5, 7, 287, 805, 435/21; 436/513, 527, 531, 548, 807, 808, 824; 422/56-58

[56] References Cited

U.S. PATENT DOCUMENTS

| | | |
|---|---|---|
| 3,615,222 | 10/1971 | Mead . |
| 3,645,687 | 2/1972 | Nerenberg . |
| 3,715,192 | 2/1973 | Wenz . |
| 3,811,840 | 5/1974 | Bauer . |
| 3,825,410 | 7/1974 | Bagshawe . |
| 3,843,324 | 10/1974 | Edelman . |
| 3,888,629 | 6/1975 | Bagshawe . |
| 3,966,897 | 6/1976 | Renn . |
| 4,039,652 | 8/1977 | Adams . |
| 4,053,284 | 10/1977 | Posch . |
| 4,061,468 | 12/1977 | Lange . |
| 4,094,647 | 6/1978 | Deutsch . |
| 4,125,372 | 11/1978 | Kawai . |
| 4,138,474 | 2/1979 | Updike . |
| 4,153,675 | 5/1979 | Kleinerman . |
| 4,168,146 | 9/1979 | Grubb . |
| 4,180,383 | 12/1979 | Johnson . |
| 4,193,983 | 3/1980 | Ullman . |
| 4,200,690 | 4/1980 | Root . |
| 4,235,601 | 11/1980 | Deutsch . |
| 4,246,339 | 1/1981 | Cole . |
| 4,298,685 | 11/1981 | Parikh ................................ 435/7 |
| 4,305,924 | 12/1981 | Piasio . |
| 4,358,535 | 11/1982 | Falkow ............................... 435/6 |
| 4,366,241 | 12/1982 | Tom . |
| 4,376,110 | 3/1983 | David . |
| 4,391,904 | 7/1983 | Litman . |
| 4,424,279 | 1/1984 | Bohn . |
| 4,425,438 | 1/1984 | Bauman . |
| 4,427,769 | 1/1984 | Adlercreutz . |

*Primary Examiner*—Sidney Marantz
*Attorney, Agent, or Firm*—William L. Respess; Ronni L. Sherman

[57] ABSTRACT

Disclosed herein is an apparatus and process for conducting ligand receptor assays. The apparatus comprises a first member which is a membrane or a filter to which is bound a receptor for the ligand or which is capable of extracting cells carrying the ligand from a fluid sample. The apparatus further comprises a second member which is composed of absorbent material which acts when in contact with the first member to induce flow through the first member when a fluid sample is added to it. The apparatus is used to conduct assays by applying a sample to the upper surface of the first member to bind ligand in the sample by means of receptor fixed to the first member or, in certain cases, by extracting cellular material which has ligand associated with it. Addition of the sample is typically followed by addition of labeled antibody against the antigen being assayed followed by a washing step to remove unbound labeled receptor. The presence of labeled antibody on the first member after washing is indicative of the presence of the antigen in the sample being assayed. In a preferred embodiment of the invention, the ligand is an antigen and the receptor is an antibody.

140 Claims, 2 Drawing Figures

METHOD AND APPARATUS FOR IMMUNOASSAYS

REFERENCE TO RELATED APPLICATION

This application is a continuation-in-part of application Ser. No. 609,395, filed May 11, 1984, U.S. Pat. No. 4,632,901, the disclosure of which is incorporated by reference.

FIELD OF THE INVENTION

This invention relates to ligand-receptor immunoassays. In particular, it relates to immunoassay processes, and, most particularly, to those using monoclonal antibodies. In another aspect it relates to an apparatus for conducting such assays.

BACKGROUND

For nearly two decades, immunoassay procedures have provided sensitive diagnostic tools for the in vitro detection of a variety of antigens associated with disease or other physical conditions of clinical significance. Originally such heterogeneous assays used a polyclonal antibody preparation bound to the solid phase. In these assays, a solution of labeled antigen is allowed to compete directly with antigen in the sample being analyzed for the solid phase antibody or is added to the antibody in a sequential process. The extent to which the labeled antigen is bound to the solid phase or is detected in the liquid phase can be used as a measure of the presence and quantity of antigen in the sample being analyzed.

Subsequently, non-competitive immunometric assays became available. In these assays, a polyclonal antibody preparation bound to a solid phase was also used. The sample containing the suspected antigen was allowed to contact the solid phase in order for the antigen to bind to the antibodies on the solid phase. Typically, after an incubation step the sample was separated from the solid phase which was then washed and incubated with a solution of additional polyclonal antibodies which had been labeled, for example with a radionuclide, an enzyme, or a fluorescent moiety.

After this second incubation, the unbound labeled antibody was separated from the solid phase and the amount of labeled antibody in either the liquid phase or bound to the solid phase in an antibody:antigen:antibody sandwich was determined as a measure of the presence and/or concentration of antigen in the sample tested.

More recently, immunoassay procedures have been modified to use monoclonal antibodies. For example, U.S. Pat. No. 4,376,110 describes two-site immunometric assays using pairs of monoclonal antibodies, one bound to a solid phase and the other labeled to permit detection. The use of monoclonal antibody pairs which recognize different epitopic sites on an antigen has made it possible to conduct simultaneous immunometric assays in which the antigen and labeled antibody incubations do not require the intermediate washing steps of prior processes.

In the foregoing processes, the solid phase antibody is typically bound to a bead or small particles or coated on a surface. All of these processes characteristically require an incubation period with both the solid phase and labeled antibodies and, as a result, are time consuming even if conducted simultaneously. In fact, it is not unusual for an assay procedure to require several hours to complete. Furthermore, the need to adhere to time incubation steps and plural washings with measured reagents has largely limited these procedures to large hospital and reference clinical laboratories where highly trained personnel and sophisticated equipment are available to perform the assays. As a result, there has gone unmet a need for a simple and rapid procedure for conducting immunoassays which employ a relatively simple apparatus to make such assays available for use in the physician's office and even for over-the-counter sale to lay persons for use in home health care programs.

SUMMARY OF THE INVENTION

The present invention provides a process for simply and rapidly performing ligand-receptor assays, for example immuno- and immunometric assays and assays which exploit the hybridization of nucleic acid oligomers which uses a simple apparatus and which does not require lengthy incubation steps. The apparatus of the invention comprises, as a first member, a porous member such as a membrane or filter to which is bound or fixed a receptor for the target analyte (ligand) being assayed, or to which is bound or fixed anti-receptor, or which is capable of separating from the sample being analyzed cells or cellular debris with which the ligand being assayed is associated to thereby fix the ligand to the porous member. For example, in the case of immuno- and immunometric assays in which the ligand is an antigen, an antibody, preferably a monoclonal antibody, is bound to the porous member as the receptor. The apparatus further comprises, as a second member, an absorbent member having capillary pathways therethrough generally transverse to its upper and lower surfaces. As used herein, the term "capillary" includes a capillary or other channel or pathway which permits a liquid to traverse the absorbent member. The second member is in capillary communication with the porous first member and is selected to have a capillary pore size so as to induce flow of liquid through the first member without the use of external means when the hydrostatic pressure of the sample and subsequent addends used in the assay are not sufficient to induce flow through the first member. The second member may also provide support for the first member.

The assay of the present invention comprises the steps of adding a liquid sample to the porous member whereby, as the liquid flows through the member, either receptor bound to the porous member binds soluble or suspended ligand in the sample at a rate that is substantially faster than the rate observed in the absence of flow through the member or, if the ligand is on the surface of cellular material, the cellular material is either bound by receptor fixed to the porous member or is entrapped by the member as the sample flows through. In a preferred embodiment of the invention, the addition of sample is followed by addition of a solution of another receptor for the ligand which is labeled to permit detection. For example, in an immunometric assay for antigen, a solution of antibody, preferably monoclonal antibody which binds the antigen at an epitope which does not interfere with binding of the first receptor, is used. The preferred label is an enzyme although other labels, for example, a radionuclide or a fluorescent label may also be used. The antibody binds to the antigen previously extracted from the sample, either by the bound antibody or by entrapment of cellular material. The addition of labeled antibody may be followed immediately, or after a brief incubation to increase sensitivity by permitting greater binding of antigen and labeled antibody, by a washing step to remove unbound labeled antibody. The presence of labeled antibody on the porous member is then determined as an indication of the presence of the target antigen in the sample. In the case of an enzyme label this is done by addition of a solution of a color forming substrate to the porous member to allow the substrate to react with the enzyme.

DESCRIPTION OF PREFERRED EMBODIMENTS

As noted above, the apparatus of the present invention comprises, as a first member, a porous membrane or filter to which is bound receptor for a ligand or to which is bound anti-receptor or which is capable of filtering cellular material from a sample being assayed if the ligand is associated with the cellular material. In the last case, the membrane or filter is selected to have a pore size which permits this separation. Any of a variety of filtering members may be used including glass fiber filters and filters of various synthetic or natural materials.

When the porous member has receptor bound to it, the receptor is selected for its ability to selectively bind directly with the target ligand. For example, if the ligand is an antigen, the receptor may be an antibody, preferably a monoclonal antibody. If the target ligand is an antibody, the receptor may be an antigen or anti-antibody. If the ligand is an enzyme, the receptor may be receptor for the enzyme. If the ligand is a nucleic acid, for example, RNA or DNA, the receptor may be a complementary oligomer of DNA or RNA. In a preferred embodiment the first member is a membrane or filter to which an antibody preparation is covalently bound. Preferably the antibody preparation comprises a monoclonal antibody even though polyclonal antibodies from antisera may be used. Techniques for polyclonal and monoclonal antibody preparation are now well known and require no citation here.

The material of the porous member is selected from a material to which the receptor or, if used, anti-receptor can be bound. In the case of protein receptors or anti-receptors, e.g., antibodies or antigens, a preferred material is nylon which has amino group residues or into which such groups have been introduced by chemical means, which permit a protein to be coupled to it by the well known glutaraldehyde method. Antibodies can be coupled to glass fibers through aminosilanes. Other natural or synthetic materials which can be coupled directly or through intermediates to a receptor may also be used.

The foregoing stresses chemical binding of the receptor or anti-receptor to the porous member. However, in appropriate cases the receptor or anti-receptor may be coated on the porous member or be a particulate which is entrapped within the interaction of the porous member. Therefore, as used herein, the term "bound" is intended to embrace any means for fixing receptor or anti-receptor to the porous member.

The second member is an absorbent member having capillary passageways generally transverse to the upper and lower surfaces. The second member is assembled with the first in a manner which permits direct communication between the pores or interstices of the first member and the capillaries of the second. Thus, as a liquid is applied to the first member and saturates it, the liquid is drawn into the absorbent member. As a result, flow can be induced through the first member when a liquid sample is applied to the upper surface of the first member even though the hydrostatic pressure of the fluid is so low that unaided it could not flow through the first member without the application of pressure to force it through or a vacuum to draw it through.

The selection of material for the second member is not critical and a variety of fibrous filter materials can be used. A useful material is cellulose acetate fibers oriented as in a cigarette filter. Those skilled in the art will appreciate that other absorbent members made of polyester, polyolefin or other materials may be used in place of cellulose acetate.

Figure 1:
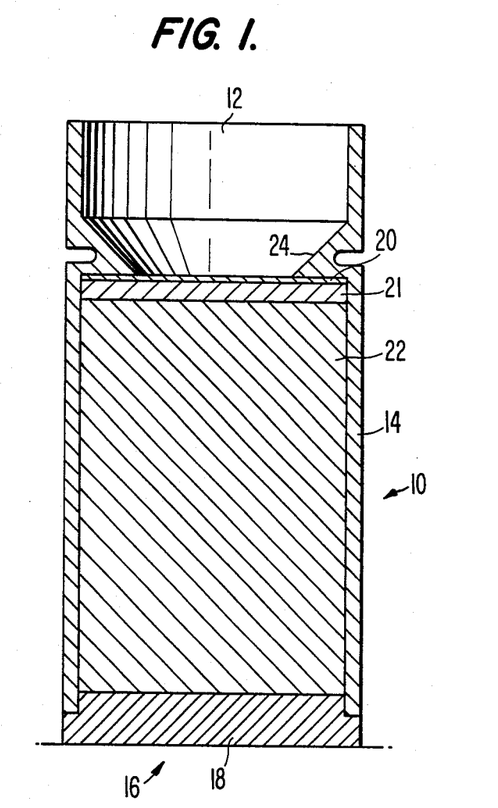
FIG. 1 is a cross-section of an apparatus for performing an immunoassay in accordance with the present invention.

Turning now to FIG. 1, there is shown in cross-section a device which can be used with the apparatus of this invention to perform the assays. Thus, in FIG. 1, a cylindrical container 10 although it may have any other appropriate shape is provided having an upper opening 12 defined by sidewall 14. The container may be made of glass, plastic, or other suitable material. As shown in FIG. 1, container 10 also has a lower opening 16, in which is inserted a removable plug 18, to permit insertion of the porous member 20, a circular membrane or filter disc, and an optional member 21, whose function is described below, which rest on cylindrical absorbent member 22, which is also inserted through opening 16.

A portion of container 10 is constricted as shown in FIG. 1 by reference numeral 24 to provide an integral funnel to direct sample onto the member 20 and to assure that effective washing of sample and other addends onto the member 20 is accomplished.

The size of member 22 and, therefore, the volume of the portion of container 10 below the constriction is preferably selected so that all of the liquid to be added to the apparatus during an assay can be received in and retained in absorbent member 22. Means for venting air (not shown in FIG. 1), for example, small ports, is provided in container 10, near the bottom, to allow displaced air to escape. Optionally, the bottom of container 10 can be eliminated and liquid allowed to pass through members 20 and 22 and exit the container through the bottom. However, since the article is intended to be disposable and to facilitate the disposal of sample in a simple and hygienic fashion, it is preferred to use a structure shown in FIG. 1.

As previously noted, member 20 may be used to either filter cellular material from a sample or as a support for bound receptor against the ligand being assayed. In either case, the liquid sample may be applied to the member 20 by introduction through opening 12. After it permeates the member 20 and the liquid is drawn therethrough by and into absorbent member 22, a solution of labeled receptor is added through opening 12 to member 20.

The labeled receptor then binds either to ligand bound to receptor on the member 20 or associated with cellular material trapped on the surface of 20. In the case of an immunometric assay, if member 20 has a monoclonal antibody bound to it, and the labeled antibody is also a monoclonal antibody, the two antibodies are selected to bind to non-interfering antigen binding sites as described in U.S. Pat. No. 4,376,110 and application Ser. No. 323,498 filed June 6, 1981, the disclosures of which are incorporated by reference.

Preferably the soluble receptor is labeled with an enzyme although other conventional assay labels may be used in appropriate circumstances. For example, a fluorescent label such as fluorescein or phycoerythrin or a radionuclide can also be used. Useful labels also include microspheres loaded with a colored dye or with a fluorescent particle. Among other useful labels may be mentioned liposomes or other vesicles loaded with a colored dye or fluorescent particles.

After the labeled receptor solution has passed through the member 20, a washing liquid is applied to member 20 to flush unbound labeled receptor from member 20 and into member 22. The sloping structure of the walls 24 provides an integral funnel to facilitate application of the washing liquid to the walls to remove adhered residue of the labeled receptor solution.

The addition of labeled receptor solution and washing liquid to the member 20 may be preceded by brief incubation periods to permit more extensive binding by receptor or ligand in solutions trapped on, or in the interstices of member 20 and, thereby, increase the sensitivity of the assay. We have found, however, that such incubation steps are either unnecessary or may be very brief, i.e., generally on the order of 60 seconds or less. The flow of solutions containing ligand or labeled receptor through the member 20 results in a substantially faster rate of binding than is observed in the absence of flow.

If the receptor label is an enzyme, after washing to remove unbound receptor from member 20, a solution of the enzyme substrate is added to member 20. If the target ligand is bound either to receptor bound to member 20 or to cellular material on member 20, the ligand will have bound to it a portion of labeled receptor. The enzyme will cause the substrate to react and generate, if properly selected, a visual color change.

We have found that when cellulose acetate is used as the material for the absorbent member 22 it may bind labeled receptor non-specifically at its upper surface. Accordingly, some visual color change may occur at this surface just under the member 20. To avoid this color change being visualized through member 20, a separating member (designated 21 in FIG. 1) of porous polyethylene or other material which does not bind receptor non-specifically is preferably disposed between members 20 and 22.

Figure 2:
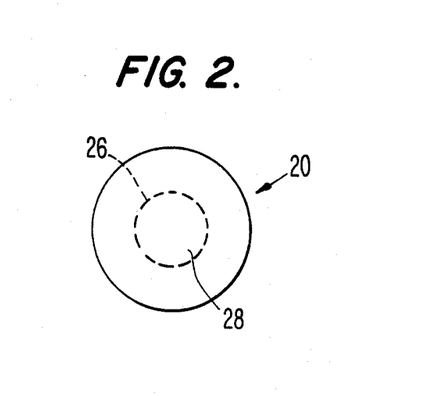
FIG. 2 is a top view of a porous member used in the invention for removing antigen from a sample being assayed.

Turning now to FIG. 2, there is shown a top view of member 20. The phantom line 26 represents the outer circumference of the area 28 in which ligand is bound in a preferred embodiment. This area has a diameter less than the diameter of the restriction formed by walls 24 at its narrowest point. Thus, when an enzyme is used as the receptor label the following results may occur: (1) the development of more color in the area 28 than in the periphery of member 20 will be read as a positive result; (2) if no color development is observed in member 20, a negative result is read; (3) if after washing some labeled receptor remains in the member 20, a modest color change which is uniform over the entire visible surface may occur. Such result is also interpreted as negative.

The foregoing is a general description of the apparatus and process of the invention. We have found it useful in performing immunoassays from introduction of sample to reading a positive result in less than five minutes. Thus, in a specific example, a monoclonal antibody against human choriogonadotropin (HCG), an antigen which is elevated in the urine of pregnant women, is bound to a porous nylon membrane using the glutaraldehyde technique and placed in a container such as 10 in FIG. 1 and supported there by an absorbent member of cellulose acetate but separated therefrom by a disc of porous polyethylene.

Samples of urine (4 ml containing 0 and 50 mIU/ml of HCG) were added to the apparatus described and drawn through members 20 and 21 into the absorbent material 22. Three (3) drops of a solution of second monoclonal antibody against HCG to which is bound alkaline phosphatase were then added. After a brief incubation, about 1 minute, during which time the conjugate is drawn through member 20, 4 ml of water was added to remove unbound antibody from member 20. This addition was followed by three drops of a solution containing indoxyl phosphate, a substrate for alkaline phosphatase. After two minutes no color developed in the device used to test the sample containing no HCG (0 mIU/ml). For the 50 mIU/ml HCG sample a distinct blue color developed in the center of the disc within thirty seconds which became dark blue within two minutes. No color developed in the periphery of the disc. The entire assay consumed about five (5) minutes. It will be appreciated that the sensitivity of the assay may be adjusted by varying the volume or incubation times.

Although the invention has been described using an assay for HCG as an example, it will be appreciated that a similar assay for other antigens may be constructed. The entire list of target antigens is too lengthy to be listed, but antigens such as IgE, prostatic acid phosphatase, prostate specific antigen, alphafetoprotein, carcinoembryonic antigen, leutenizing hormone, creatine kinase MB and other antigens in serum, plasma, urine or other liquid media may be detected. Additionally, liquid samples containing material having antigens associated therewith such as antigens associated with bacteria, parasites, fungi, or viruses including, for example, group A and B streptococcus, *Neisseria gonorrhea, Gardnerella vaginalis, Trichomonas vaginalis, Candida albicans, Chlamydia trachomatis*, hepatitis B, and cytomegalovirus can be detected by using a filter which will trap the cells or a filter to which antibody specific for the antigen is bound as member 20. Addition of a solution of a monoclonal antibody labeled, for example, with an enzyme, will result in binding of the antibody to the antigen. Washing and substrate addition will result in the color change associated with presence of the labeled antibody on the cells, which can be detected visually or by aid of an instrument.

If a label other than an enzyme is used, the procedure may be varied. Fluorescence of the membrane could be measured if a fluorescing label is used. If a radionuclide label such as $^{125}$I is used, the membrane can be removed and counted.

The foregoing has stressed the application of the invention to sequential immunometric assays with monoclonal antibodies, i.e., an immunoassay using a first monoclonal antibody receptor on the porous member and a second monoclonal antibody receptor which is labeled. Sample is added to the porous member followed by labeled antibody. Other assay variants are possible. For example, in the case of an immunometric assay, the labeled antibody and sample may be admixed prior to addition to the porous member.

The apparatus of this invention may also be used in assays for an antibody which employ an antigen as first receptor on the solid phase and which use labeled antigen or labeled anti-antibody as the second receptor. The latter is particularly suited to allergy specific assays where the first receptor is an allergen bound to the porous member and the second receptor is an antibody, preferably a monoclonal antibody, to IgE. In other cases, the IgG response to allergens may be measured similarly, i.e., by using an antibody, such as a monoclonal antibody against IgG, as the second receptor. Other antibody tests which can be carried out in this manner include tests for antibodies to herpes, rubella, hepatitis, cytomegalovirus and HTLV-III.

In another embodiment of the invention, the apparatus is used to perform competitive assays, i.e., assays in which the ligand receptor is bound to the porous member and for which the ligand in the sample competes with a fixed quantity of labeled ligand added to the sample solution or added following sample addition. Competitive immunoassays are conveniently run in this fashion using an antibody, for example, a monoclonal or polyclonal antibody preparation as receptor bound to the solid phase. Labeled antigen can be added to the sample before the sample is added to the porous memer. Alternatively, it can be added subsequent to addition of the sample or concurrently therewith.

The apparatus of the invention can also be used to detect an enzyme by binding the enzyme's receptor to the porous member as the assay receptor. A labeled antibody against the enzyme can be used to detect formation of a receptor-enzyme complex on the porous member.

The porous member can also be based with a nucleic acid oligomer as a probe-receptor for nucleic acid material in a sample. The probe may be an oligomer of DNA, for example, complementary to a sequence in the nucleic acid of interest and can be used to bind either RNA or DNA as ligand as the case may be. Detection of the ligand-receptor complex can be done using a second nucleic acid oligomer complementary to a noninterfering region of the nucleic acid ligand of interest, the second oligomer being labeled to permit detection.

In yet another embodiment of the invention, the porous member may have anti-receptor bound to it. As used herein, the term "anti-receptor" is intended to refer to agents which will bind selectively to the receptor of a ligand-receptor pair. For example, if the ligand is an antigen and the receptor is an antibody, for example, a mouse IgG antibody (preferably a monoclonal antibody), the anti-receptor may be an antibody, preferably a monoclonal antibody, against murine IgG. In other cases the receptor may be conjugated with a moiety which binds selectively with the anti-receptor. For example, the moiety may be a hapten and the anti-receptor an antibody against the hapten. A preferred such hapten is fluorescein. In other cases, the anti-receptor may be avidin. In that case, the receptor will have biotin bound to it. In other cases, the receptor may be nucleic acid oligomer, or have such an oligomer bound to it, and the anti-receptor may be a nucleic acid segment complementary to a portion of the receptor oligomer which does not impair receptor binding with the ligand. Those skilled in the art will appreciate from the foregoing that a variety of anti-receptor:receptor combinations may be employed.

When an anti-receptor is used, the sample may be assayed in a variety of ways. For example, in a "sandwich assay" first receptor and second, labeled receptor may be combined with the sample to bind ligand prior to addition to the porous member. Alternatively, first receptor and sample may be combined prior to addition to the porous member, or added in the sequence first receptor then sample, to be followed by addition of labeled receptor. In such sandwich assays, the anti-receptor is selected to bind the first receptor and not the labeled receptor.

The use of an anti-receptor bound to the porous member makes it possible to simplify development and preparation of the porous member useful in ligand-receptor assays. For example, if receptor is bound to the porous member, it may be necessary to modify the binding procedure in order to optimize the binding of each receptor required for a panel of assays. However, a single anti-receptor bound to the porous member may be employed in a plurality of assays. As a result, the development effort and manufacturing procedures may be greatly simplified when such a "universal" porous member is possible.

We claim:

1. An apparatus for use in a ligand-receptor assay process for determination of the presence or concentration of a target ligand in a liquid sample comprising:
   (a) a porous first member which has upper and lower surfaces, the sample being applied to the upper surface, and wherein at least one first receptor capable of binding the target ligand is directly or indirectly bound within an area smaller than the area of the member to which the sample is applied; and
   (b) a second member which is a body of absorbent material having a surface over which the lower surface of the first member is placed and having capillaries therethrough which are in communication with the pores on the lower surface of the first member so as to draw liquid added to the upper surface of the first member which has permeated the first member into the capillaries of the second member, the communication between the first and second members having been established prior to, and maintained during, addition of liquids to the apparatus during the assay process.

2. An apparatus according to claim 1 wherein the target ligand is selected from the group consisting of antigens, antibodies, enzymes, and nucleic acid oligomers.

3. An apparatus according to claim 2 wherein the first receptor is selected from the group consisting of antibodies, antigens, enzyme receptors, and nucleic acid oligomers.

4. An apparatus according to claim 1 wherein the porous first member is a membrane or filter.

5. An apparatus according to claim 4 wherein the membrane or filter is of a material selected from glass or nylon.

6. An apparatus according to claim 4 wherein the first and second members are separated by at least one porous member.

7. An apparatus according to claim 4 wherein the apparatus further comprises a container for the first and second members having an opening sufficient to permit the application of assay reagents to the first member.

8. An apparatus according to claim 7 wherein the opening further comprises a section having sides which slope inwardly to define a funnel for direction of the assay reagents applied to the first member.

9. An apparatus according to claim 7 wherein the bottom end of the container is closed and the container is of a volume sufficient to contain all of the assay reagents applied to the first member during the assay, the container being vented to allow escape of displaced air.

10. An apparatus according to claim 9 wherein the apparatus is disposable.

11. An apparatus according to claim 9 wherein a signal is generated to indicate the presence or concentration of the target ligand following the application of the assay reagents to the first member, the signal being either visual or determined by instrumental means.

12. An apparatus according to claim 11 wherein the signal is visual.

13. An apparatus according to claim 11 wherein the signal is generated within about five minutes following the application of the assay reagents to the first member.

14. An apparatus according to claim 13 wherein the signal is visual.

15. An apparatus according to claim 1 wherein the assay is a nucleic acid probe assay.

16. An apparatus according to claim 15 wherein the first receptor is a nucleic acid oligomer.

17. An apparatus according to claim 16 wherein the nucleic acid oligomer is a DNA oligomer.

18. An apparatus according to claim 1 wherein the assay is an immunoassay.

19. An apparatus according to claim 18 wherein the first receptor is an antibody.

20. An apparatus according to claim 19 wherein the antibody is a polyclonal antibody preparation.

21. An apparatus according to claim 19 wherein the antibody is a monoclonal antibody.

22. An apparatus according to claim 18 wherein the first receptor is an antigen.

23. An apparatus according to claim 20 wherein the target ligand is human choriogonadotropin.

24. An apparatus according to claim 21 wherein the target ligand is human choriogonadotropin.

25. An apparatus according to claim 20 wherein the target ligand is an antigen associated with group A or group B streptococcus.

26. An apparatus according to claim 21 wherein the target ligand is an antigen associated with group A or group B streptococcus.

27. An apparatus according to claim 18 wherein the target ligand is an antigen or antibody associated with a virus.

28. An apparatus according to claim 27 wherein the virus is a hepatitis virus.

29. An apparatus according to claim 27 wherein the virus is associated with AIDS.

30. A ligand-receptor assay process for determination of the presence or concentration of a target ligand in a liquid sample employing the apparatus of claim 1 comprising:
   (a) applying the liquid sample suspected of containing the target ligand to the upper surface of the porous first member of the apparatus;
   (b) applying to the upper surface a second receptor capable of binding the target ligand, the second receptor being labeled to permit its detection;
   (c) separating unbound labeled second receptor from any labeled second receptor bound to the target ligand within the first member; and
   (d) determining the presence or concentration of the target ligand by detection of bound labeled second receptor.

31. A ligand-receptor assay process for determination of the presence or concentration of a target ligand in a liquid sample employing the apparatus of claim 1 comprising:
   (a) mixing the liquid sample suspected of containing the target ligand with a second receptor capable of binding the target ligand, the second receptor being labeled to permit its detection;
   (b) applying the mixture of the liquid sample and the labeled second receptor to the upper surface of the porous first member of the apparatus;
   (c) separating unbound labeled second receptor from any labeled second receptor bound to the target ligand within the first member; and
   (d) determining the presence or concentration of the target ligand by detection of bound labeled second receptor.

32. A process according to claims 30 or 31 wherein the target ligand is selected from the group consisting of antigens, antibodies, enzymes, and nucleic acid oligomers.

33. A process according to claim 32 wherein the first receptor is selected from the group consisting of antibodies, antigens, enzyme receptors and nucleic acid oligomers.

34. A process according to claims 30 or 31 wherein separation of unbound second labeled receptor from the first member is accomplished by washing.

35. A process according to claim 34 wherein the second labeled receptor is labeled with an enzyme and the washing step is followed by application to the first member of a substrate for the enzyme, the enzyme and substrate being selected to generate a color change which is either visual or determined by instrumental means.

36. A process according to claim 35 wherein the color change is visual.

37. A process according to claims 30 or 31 wherein the assay is a nucleic acid probe assay.

38. A process according to claim 37 wherein the target ligand is a nucleic acid oligomer and the first and second receptors are complementary nucleic acid oligomers.

39. A process according to claim 38 wherein the first and second receptors are DNA oligomers.

40. A process according to claim 39 wherein the target ligand is a DNA oligomer.

41. A process according to claim 39 wherein the target ligand is an RNA oligomer.

42. A process according to claims 30 or 31 wherein the assay is an immunoassay.

43. A process according to claim 42 wherein the target ligand is an antigen and the first and second receptors are antibodies.

44. A process according to claim 43 wherein at least one of the antibodies is a polyclonal antibody preparation.

45. A process according to claim 43 wherein at least one of the antibodies is a monoclonal antibody.

46. A process according to claim 45 wherein the first and second antibodies are monoclonal antibodies which bind, respectively, to non-interfering epitopes of the antigen.

47. A process according to claim 42 wherein the target ligand is an antibody and at least one of the first and second receptors is an antigen.

48. A process according to claim 47 wherein the target ligand is an antibody, the first receptor is an antigen, and the second receptor is an antibody against the target antibody.

49. A process according to claim 48 wherein the antigen is an allergen and the target antibody is an IgE antibody.

50. A process according to claim 49 wherein the antibody against the IgE antibody is an anti-IgE monoclonal antibody.

51. A process according to claim 44 wherein the target ligand is human choriogonadotropin.

52. A process according to claim 45 wherein the target ligand is human choriogonadotropin.

53. A process according to claim 46 wherein the target ligand is human choriogonadotropin.

54. A process according to claim 44 wherein the target ligand is an antigen associated with group A or group B streptococcus.

55. A process according to claim 45 wherein the target ligand is an antigen associated with group A or group B streptococcus.

56. A process according to claim 46 wherein the target ligand is an antigen associated with group A or group B streptococcus.

57. A process according to claim 42 wherein the target ligand is an antigen or antibody associated with a virus.

58. A process according to claim 57 wherein the virus is a hepatitis virus.

59. A process according to claim 57 wherein the virus is associated with AIDS.

60. A process according to claim 42 wherein the liquid sample is urine, serum, plasma, or other liquid media.

61. An apparatus for use in a ligand-receptor assay process for determination of the presence or concentration of a target ligand in a liquid sample comprising:
  (a) a porous first member which has upper and lower surfaces, the sample being applied to the upper surface, and wherein at least one anti-receptor capable of binding a first receptor is directly or indirectly bound within an area smaller than the area of the member to which the sample is applied, the first receptor being capable of binding the target ligand; and
  (b) a second member which is a body of absorbent material having a surface over which the lower surface of the first member is placed and having capillaries therethrough which are in communication with the pores on the lower surface of the first member so as to draw liquid added to the upper surface of the first member which has permeated the first member into the capillaries of the second member, the communication between the first and second members having been established prior to, and maintained during, addition of liquids to the apparatus during the assay process.

62. An apparatus according to claim 61 wherein the target ligand is selected from the group consisting of antigens, antibodies, enzymes, and nucleic acid oligomers.

63. An apparatus according to claim 62 wherein the first receptor is selected from the group consisting of antibodies, antigens, enzyme receptors, and nucleic acid oligomers.

64. An apparatus according to claim 61 wherein the porous first member is a membrane or filter.

65. An apparatus according to claim 64 wherein the membrane or filter is of a material selected from glass or nylon.

66. An apparatus according to claim 64 wherein the first and second members are separated by at least one porous member.

67. An apparatus according to claim 64 wherein the apparatus further comprises a container for the first and second members having an opening sufficient to permit the application of assay reagents to the first member.

68. An apparatus according to claim 67 wherein the opening further comprises a section having sides which slope inwardly to define a funnel for direction of the assay reagents applied to the first member.

69. An apparatus according to claim 67 wherein the bottom end of the container is closed and the container is of a volume sufficient to contain all of the assay reagents applied to the first member during the assay, the container being vented to allow escape of displaced air.

70. An apparatus according to claim 69 wherein the apparatus is disposable.

71. An apparatus according to claim 69 wherein a signal is generated to indicate the presence or concentration of the target ligand following the application of the assay reagents to the first member, the signal being either visual or determined by instrumental means.

72. An apparatus according to claim 71 wherein the signal is visual.

73. An apparatus according to claim 71 wherein the signal is generated within about five minutes following the application of the assay reagents to the first member.

74. An apparatus according to claim 73 wherein the signal is visual.

75. An apparatus according to claim 61 wherein the assay is a nucleic acid probe assay.

76. An apparatus according to claim 75 wherein the first receptor is a nucleic acid oligomer.

77. An apparatus according to claim 76 wherein the nucleic acid oligomer is a DNA oligomer.

78. An apparatus according to claim 61 wherein the assay is an immunoassay.

79. An apparatus according to claim 78 wherein the first receptor is an antibody.

80. An apparatus according to claim 79 wherein the antibody is a polyclonal antibody preparation.

81. An apparatus according to claim 79 wherein the antibody is a monoclonal antibody.

82. An apparatus according to claim 78 wherein the first receptor is an antigen.

83. An apparatus according to claim 80 wherein the target ligand is human choriogonadotropin.

84. An apparatus according to claim 81 wherein the target ligand is human choriogonadotropin.

85. An apparatus according to claim 80 wherein the target ligand is an antigen associated with group A or group streptococcus.

86. An apparatus according to claim 81 wherein the target ligand is an antigen associated with group A or group streptococcus.

87. An apparatus according to claim 78 wherein the target ligand is an antigen or antibody associated with a virus.

88. An apparatus according to claim 87 wherein the virus is a hepatitis virus.

89. An apparatus according to claim 87 wherein the virus is associated with AIDS.

90. An apparatus according to claim 78 wherein the first receptor is an antibody and the anti-receptor is an antibody against the first receptor.

91. An apparatus according to claim 90 wherein at least one of the antibodies is a polyclonal antibody preparation.

92. An apparatus according to claim 90 wherein at least one of the antibodies is a monoclonal antibody.

93. An apparatus according to claim 92 wherein the first receptor is a monoclonal antibody.

94. An apparatus according to claim 92 wherein the anti-receptor is a monoclonal antibody.

95. An apparatus according to claim 78 wherein the first receptor is conjugated with a hapten and the anti-receptor is an antibody against the hapten.

96. An apparatus according to claim 78 wherein the hapten is fluorescein.

97. An apparatus according to claim 78 wherein the first receptor is conjugated to biotin and the anti-receptor is avidin.

98. A ligand-receptor asasy process for determination of the presence or concentration of a target ligand in a liquid sample employing the apparatus of claim 61 comprising:
 (a) applying the first receptor capable of binding the target ligand and the liquid sample suspected of containing the target ligand to the upper surface of the porous first member of the apparatus;
 (b) applying to the upper surface a second receptor capable of binding the target ligand, the second receptor being labeled to permit its detection;
 (c) separating unbound labeled second receptor from any labeled second receptor bound to the target ligand within the first member; and
 (d) determining the presence or concentration of the target ligand by detection of bound labeled second receptor.

99. A ligand-receptor assay process for determination of the presence or concentration of a target ligand in a liquid sample employing the apparatus of claim 61 comprising:
 (a) applying the first receptor capable of binding the target ligand to the upper surface of the porous first member of the apparatus;
 (b) mixing the liquid sample suspected of containing the target ligand with a second receptor capable of binding the target ligand, the second receptor being labeled to permit its detection;
 (c) applying the mixture of the liquid sample and the labeled second receptor to the upper surface of the porous first member of the apparatus;
 (d) separating unbound labeled second receptor from any labeled second receptor bound to the target ligand within the first member; and
 (e) determining the presence or concentration of the target ligand by detection of bound labeled second receptor.

100. A process according to claims 98 or 99 wherein the target ligand is selected from the group consisting of antigens, antibodies, enzymes, and nucleic acid oligomers.

101. A process according to claim 100 wherein the first receptor is selected from the group consisting of antibodies, antigens, enzyme receptors and nucleic acid oligomers.

102. A process according to claims 98 or 99 wherein separation of unbound labeled receptor from the first member is accomplished by washing.

103. A process according to claim 102 wherein the second labeled receptor is labeled with an enzyme and the washing step is followed by application to the first member of a substrate for the enzyme, the enzyme and substrate being selected to generate a color change which is either visual or determined by instrumental means.

104. A process according to claim 103 wherein the color change is visual.

105. A process according to claims 98 or 99 wherein the assay is a nucleic acid probe assay.

106. A process according to claim 105 wherein the target ligand is a nucleic acid oligomer and the first and second receptors are complementary nucleic acid oligomers.

107. A process according to claim 106 wherein the first and second receptors are DNA oligomers.

108. A process according to claim 107 wherein the target ligand is a DNA oligomer.

109. A process according to claim 108 wherein the target ligand is an RNA oligomer.

110. A process according to claims 98 or 99 wherein the assay is an immunoassay.

111. A process according to claim 110 wherein the target ligand is an antigen and the first and second receptors are antibodies.

112. A process according to claim 111 wherein at least one of the antibodies is a polyclonal antibody preparation.

113. A process according to claim 111 wherein at least one of the antibodies is a monoclonal antibody.

114. An process according to claim 113 wherein the first and second antibodies are monoclonal antibodies which bind, respectively, to non-interfering epitopes of the antigen.

115. A process according to claim 110 wherein the target ligand is an antibody and at least one of the first and second receptors is an antigen.

116. A process according to claim 115 wherein the target ligand is an antibody, the first receptor is an antigen, and the second receptor is an antibody against the target antibody.

117. A process according to claim 116 wherein the antigen is an allergen and the target antibody is an IgE antibody.

118. A process according to claim 117 wherein the antibody against the IgE antibody is an anti-IgE monoclonal antibody.

119. A process according to claim 112 wherein the target ligand is human choriogonadotropin.

120. A process according to claim 113 wherein the target ligand is human choriogonadotropin.

121. A process according to claim 114 wherein the target ligand is human choriogonadotropin.

122. A process according to claim 112 wherein the target ligand is an antigen associated with group A or group B streptococcus.

123. A process according to claim 113 wherein the target ligand is an antigen associated with group A or group B streptococcus.

124. A process according to claim 114 wherein the target ligand is an antigen associated with group A or group B streptococcus.

125. A process according to claim 110 wherein the target ligand is an antigen or antibody associated with a virus.

126. A process according to claim 125 wherein the virus is a hepatitis virus.

127. A process according to claim 125 wherein the virus is associated with AIDS.

128. A process according to claim 110 wherein the liquid sample is urine, serum, plasma, or other liquid media.

129. A process according to claim 110 wherein the anti-receptor is an antibody.

130. A process according to claims 98 or 99 wherein application of the first receptor is followed by application of the liquid sample.

131. A process according to claims 98 or 99 wherein the first receptor and the liquid sample are admixed prior to application to the first member.

132. An apparatus according to claim 11 wherein the assay is an immunoassay.

133. An apparatus according to claim 132 wherein the first receptor is an antibody and the target ligand is human choriogonadotropin.

134. An apparatus according to claim 133 wherein the antibody is a monoclonal antibody.

135. An apparatus according to claim 132 wherein the first receptor is an antibody and the target ligand is an antigen associated with Group A streptococcus.

136. An apparatus according to claim 135 wherein the antibody is a monoclonal antibody.

137. A process according to claim 35 wherein the assay is an immunoassay.

138. A process according to claim 137 wherein at least one of the first and second receptors is a monoclonal antibody.

139. A process according to claim 138 wherein the target ligand is human choriogonadotropin.

140. A process accoring to claim 138 wherein the target ligand is an antigen associated with Group A streptococcus.

* * * * *

UNITED STATES PATENT AND TRADEMARK OFFICE
CERTIFICATE OF CORRECTION

PATENT NO. : 4,727,019

DATED : February 23, 1988

INVENTOR(S) : Gunars E. Valkirs, Newton C. Owen, Philip A. Levinson

It is certified that error appears in the above-identified patent and that said Letters Patent is hereby corrected as shown below:

```
Claim 96, line 18, "according to claim 78"
should read -- according to claim 95 --.

Claim 85, line 60, "group streptococcus"
should read -- group B streptococcus --.

Claim 86, line 63, "group streptococcus"
should read -- group B streptococcus --.

Claim 135, line 8, "Group A streptococcus"
should read -- group A streptococcus --.

Claim 140, line 19, "Group A streptococcus"
should read -- group A streptococcus --.
```

Signed and Sealed this

First Day of November, 1988

Attest:

DONALD J. QUIGG

Attesting Officer

Commissioner of Patents and Trademarks